(12) United States Patent
Predick

(10) Patent No.: US 9,610,100 B2
(45) Date of Patent: Apr. 4, 2017

(54) MODULAR TELESCOPING SURGICAL INSTRUMENT

(71) Applicant: Life Spine, Inc., Huntley, IL (US)

(72) Inventor: Daniel Predick, Chicago, IL (US)

(73) Assignee: Life Spine, Inc., Huntley, IL (US)

( * ) Notice: Subject to any disclaimer, the term of this patent is extended or adjusted under 35 U.S.C. 154(b) by 257 days.

(21) Appl. No.: 14/275,326

(22) Filed: May 12, 2014

(65) Prior Publication Data

US 2014/0336717 A1 Nov. 13, 2014

Related U.S. Application Data

(60) Provisional application No. 61/822,385, filed on May 12, 2013.

(51) Int. Cl.
*A61B 17/56* (2006.01)
*A61B 17/16* (2006.01)
*A61B 17/00* (2006.01)

(52) U.S. Cl.
CPC ............ *A61B 17/56* (2013.01); *A61B 17/162* (2013.01); *A61B 2017/0046* (2013.01)

(58) Field of Classification Search
CPC ............ A61B 17/56; A61B 2017/0046; A61B 2017/00991; B25G 1/04; B25G 1/043; B25G 3/06
See application file for complete search history.

(56) References Cited

U.S. PATENT DOCUMENTS

| | | | | |
|---|---|---|---|---|
| 6,530,125 B2 * | 3/2003 | Shippert | ................ | B25G 1/102 16/422 |
| 8,282,640 B2 * | 10/2012 | Hung | ..................... | A61B 17/02 606/84 |
| 2012/0253353 A1 * | 10/2012 | McBride | ............ | A61B 17/1757 606/97 |
| 2014/0275802 A1 * | 9/2014 | Gerdts | ................... | A61B 17/02 600/227 |

* cited by examiner

*Primary Examiner* — Andrew Yang
(74) *Attorney, Agent, or Firm* — Foley & Lardner LLP

(57) ABSTRACT

A surgical instrument provides rotational and axial variations of a working end relative to a handle of the surgical instrument for configuration flexibility of the working end. An internal configuration of the handle of the surgical instrument accepts a retention portion of the working end in several positions. The working end can be varied in axial length relative to a front end of the handle and in axial position relative to the extension of the working end from the front end of the handle. A retention mechanism interacts with the handle and the working end to fix a position of the working end in the handle. The working end may be shaped to provide a bayonet version wherein the working end extends from the front end of the handle offset from the handle's longitudinal center, and a non-bayonet version wherein the working end extends from the handle's longitudinal center.

12 Claims, 10 Drawing Sheets

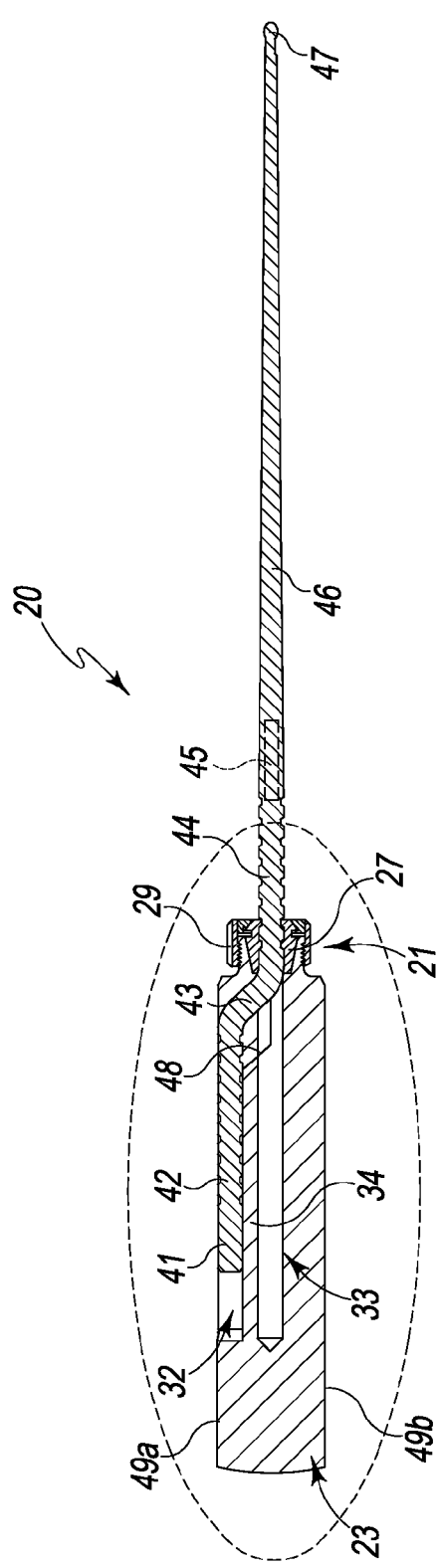
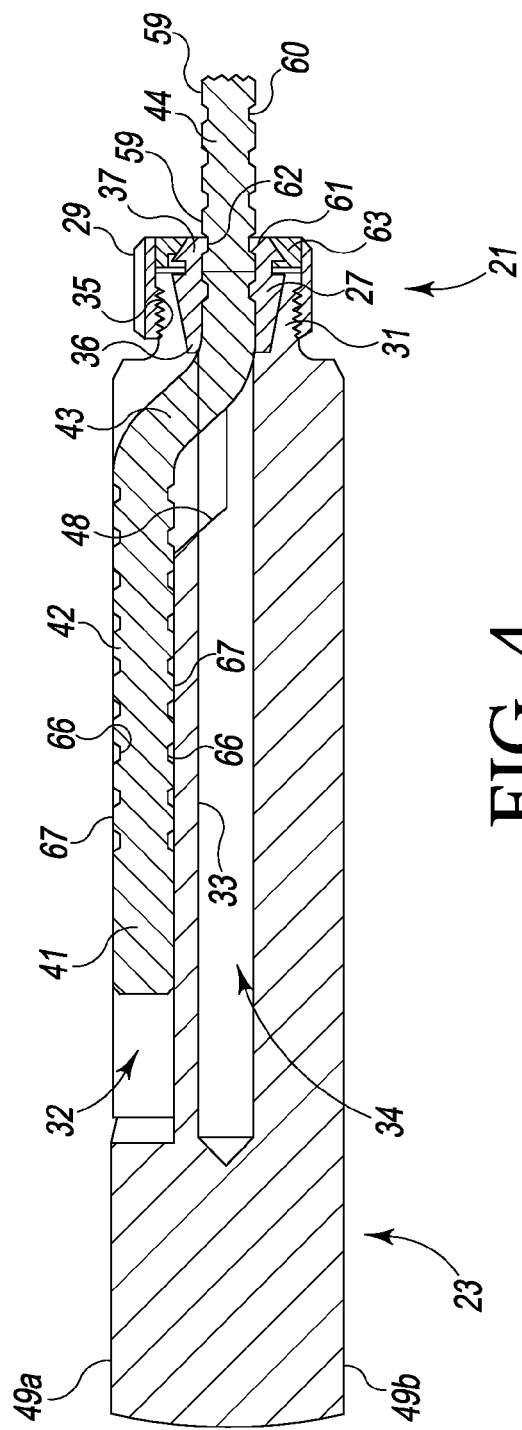
FIG. 3
FIG. 4

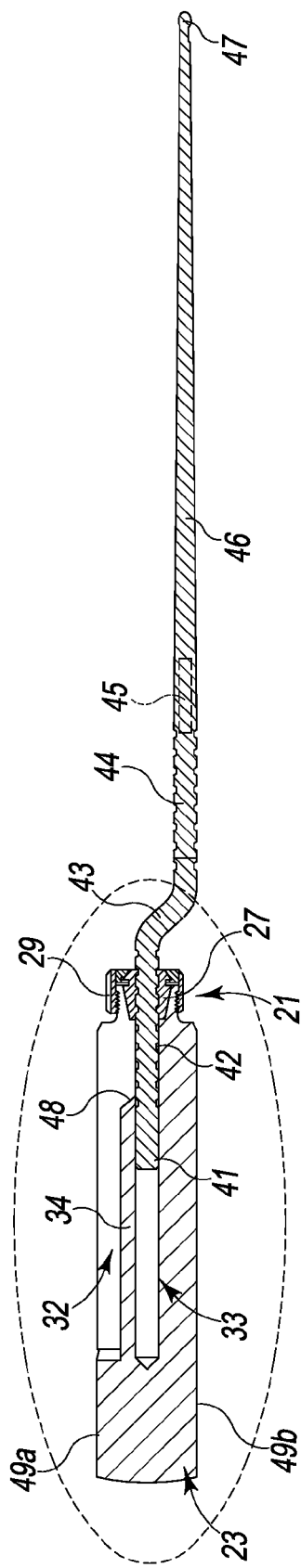
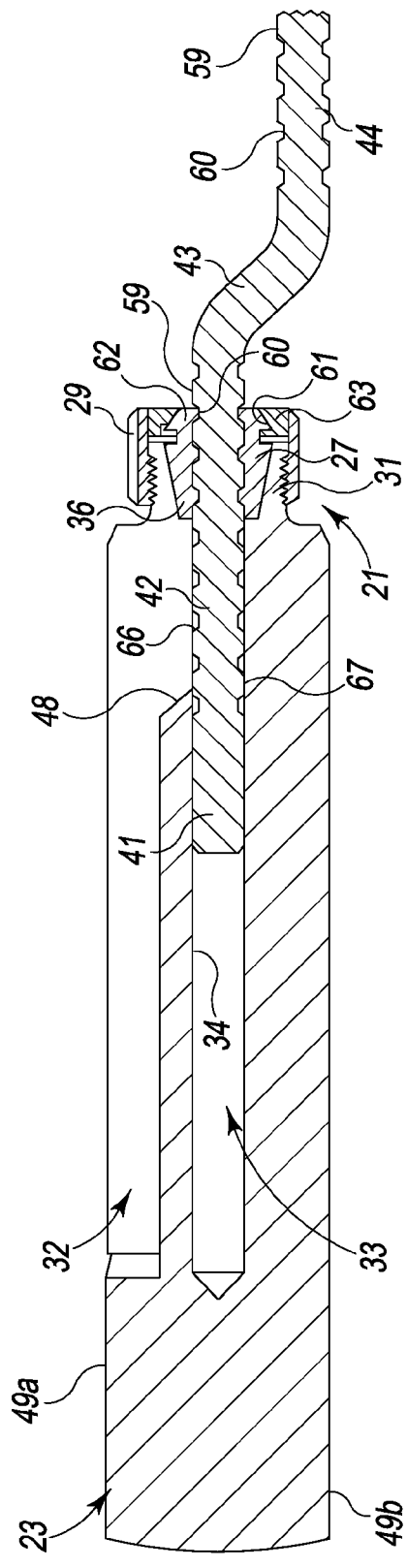
FIG. 5
FIG. 6

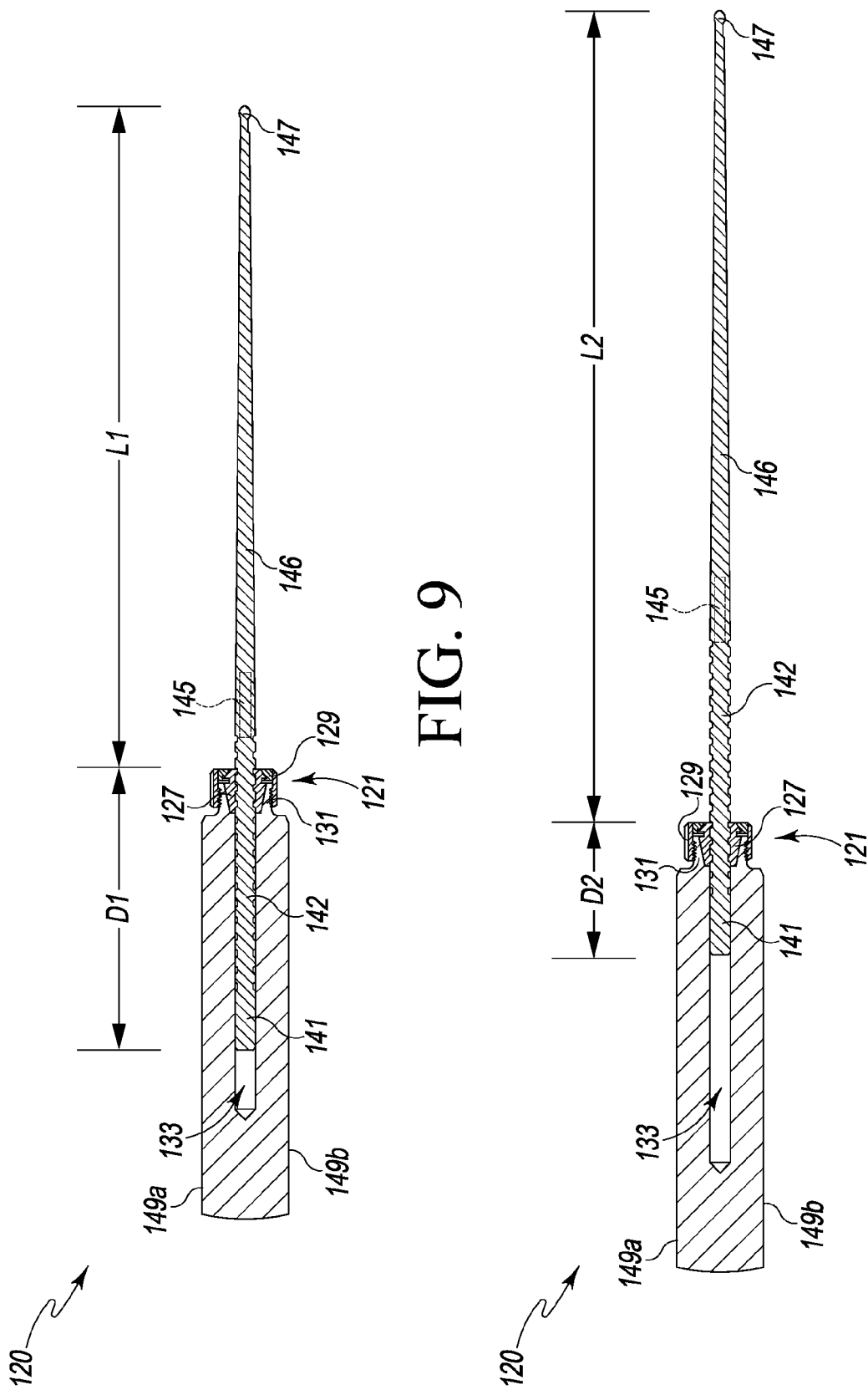

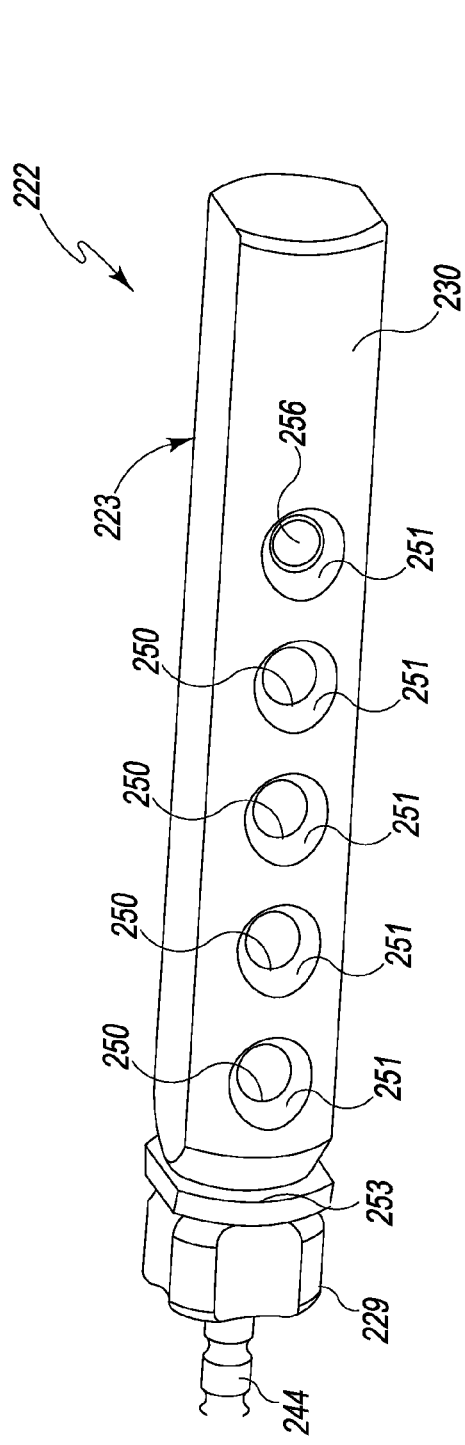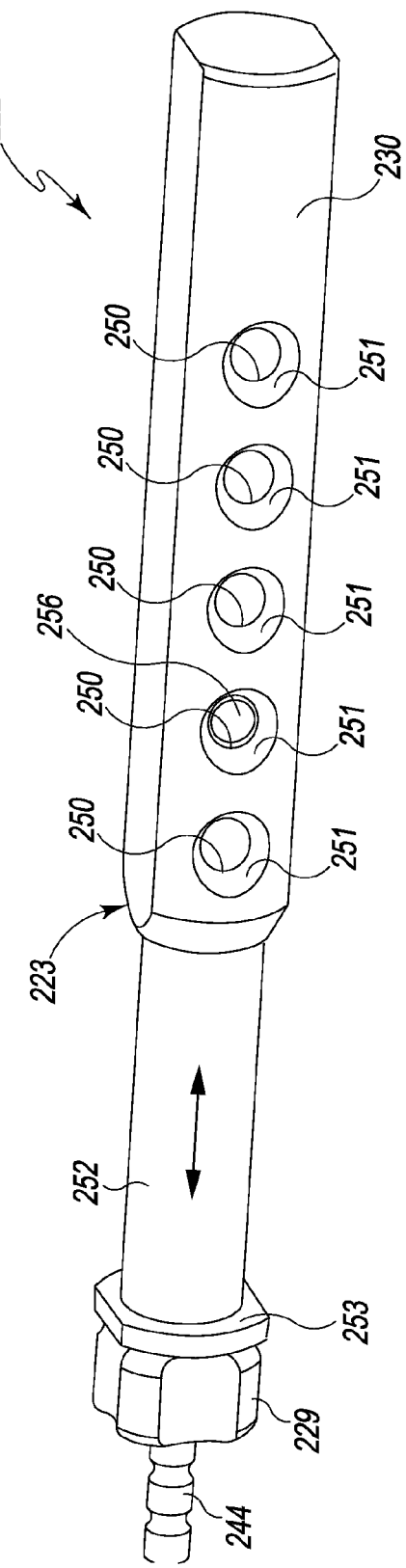
FIG. 13
FIG. 14

MODULAR TELESCOPING SURGICAL INSTRUMENT

CROSS-REFERENCE TO RELATED APPLICATIONS

This patent application claims the benefit of and/or priority under 35 U.S.C. §119(e) to U.S. Provisional Patent Application Ser. No. 61/822,385 filed May 12, 2013, entitled "Modular Telescoping Surgical Instrument" the entire contents of which is specifically incorporated herein by this reference.

BACKGROUND OF THE INVENTION

Field of the Invention

The present invention relates to surgical instruments and, more particularly, to surgical instruments for orthopedic surgery that provide configuration flexibility.

Background Information

Tools or instruments that allow flexibility in configuration in order to accommodate individual preferences for use inherently have greater utility. This is true for all types of tools or instruments for all types of purposes. Even the simplest of tools can benefit from being able to provide flexibility in configuration. Surgical tools or instruments are no exception. Configurable surgical instruments also reduce the number of instruments required for a given surgical procedure.

A surgical instrument that can accommodate a surgeon's individual preferences for use of the instrument or of use for a particular purpose would be an asset. However, many surgical instruments are static in configuration and thus do not provide configuration flexibility.

It is therefore an object of the present invention to provide a surgical instrument that provides configuration flexibility.

BRIEF SUMMARY OF THE INVENTION

The present invention comprises a modular telescoping surgical instrument. Several embodiments and mechanisms are disclosed that provide configuration flexibility and length adjustment of a working end of the modular telescoping surgical instrument relative to a handle of the modular telescoping surgical instrument.

The length of a working end of the modular telescoping surgical instrument relative to a handle of the modular telescoping surgical instrument is varied through a retention mechanism. The retention mechanism includes a constrictor that holds a configured area of a rear portion of the working end radially in and relative to the handle via a threaded knob or cap and angled inner walls of a neck of the handle. The retention mechanism allows a user to easily but securely adjust length between the handle and a working tip of the working end of the modular telescoping surgical instrument.

In one form, the modular telescoping surgical instrument is additionally convertible between a bayonet version wherein the working end extends from the handle offset from the handle center, and a non-bayonet version wherein the working end extends from the handle center.

The working end of the bayonet/non-bayonet version of the present surgical instrument has a rear portion defining a first longitudinal axis, a front portion defining a second longitudinal axis, and a crook or bend between the rear portion and the front portion whereby the second longitudinal axis is axially offset from but parallel to the first longitudinal axis. The angle of the crook or bend determines the amount of axial offset between the first and second longitudinal axes (such as a center longitudinal axis and an off-center longitudinal axis).

The constrictor may comprise a collet that radially surrounds the configured (e.g. grooved) area at a rear of the working end within a front portion or neck of the handle. The threaded knob is received on a threaded end of the neck of the handle and at the proximate end of the collet. As the threaded knob is received on the neck of the handle, the knob axially compresses the collet towards and into the internal angled walls of the neck of the front portion of the handle thereby causing axial flanges of the collet to radially compress around and against a portion of the working end to fix the working end relative to the handle.

The present invention will be more apparent upon reading the following detailed description in conjunction with the accompanying drawings.

BRIEF DESCRIPTION OF THE DRAWINGS

The above mentioned and other features and objects of this invention, and the manner of attaining them, will become more apparent and the invention itself will be better understood by reference to the following description of embodiments of the invention taken in conjunction with the accompanying drawings, wherein:

FIG. 3 is a sectional side view of the surgical instrument of FIG. 1;

FIG. 4 is an enlarged sectional side view of a circled portion of the surgical instrument of FIG. 3 particularly showing the handle of the surgical instrument;

FIG. 5 is a sectional side view of the surgical instrument of FIG. 1, the surgical instrument shown in the bayonet version;

FIG. 6 is an enlarged sectional side view of the circled portion of FIG. 5 particularly showing the handle of the surgical instrument;

FIG. 9 is a sectional side view of the surgical instrument of FIG. 7, the working end shown in a near minimum length position relative to the handle;

FIG. 10 is a sectional side view of the surgical instrument of FIG. 7, the working end shown in a near maximum length position relative to the handle;

FIG. 13 is an isometric view of a length adjustable handle for the present modular telescoping surgical instrument, the length adjustable handle shown in a minimum length position;

FIG. 14 is an isometric view of the length adjustable handle of FIG. 13 with the length adjustable handle shown in a near maximum length position;

Like reference numerals indicate the same or similar parts throughout the several figures.

Figure 1:
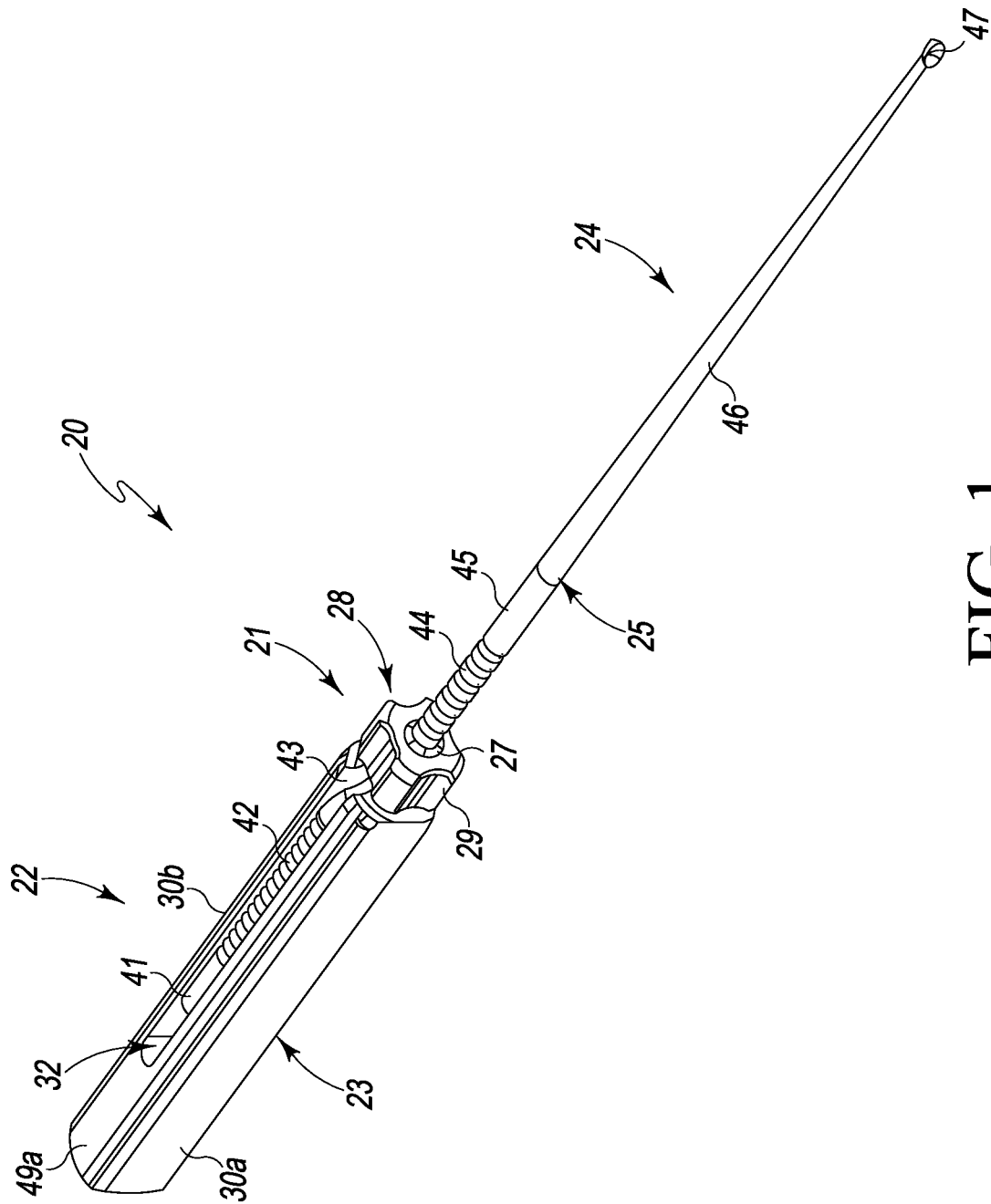
FIG. 1 is an isometric view of an exemplary embodiment of a modular, telescoping surgical instrument, wherein a working end thereof is also convertible between a bayonet version and a non-bayonet version, the surgical instrument shown in the non-bayonet version.
Figure 2:
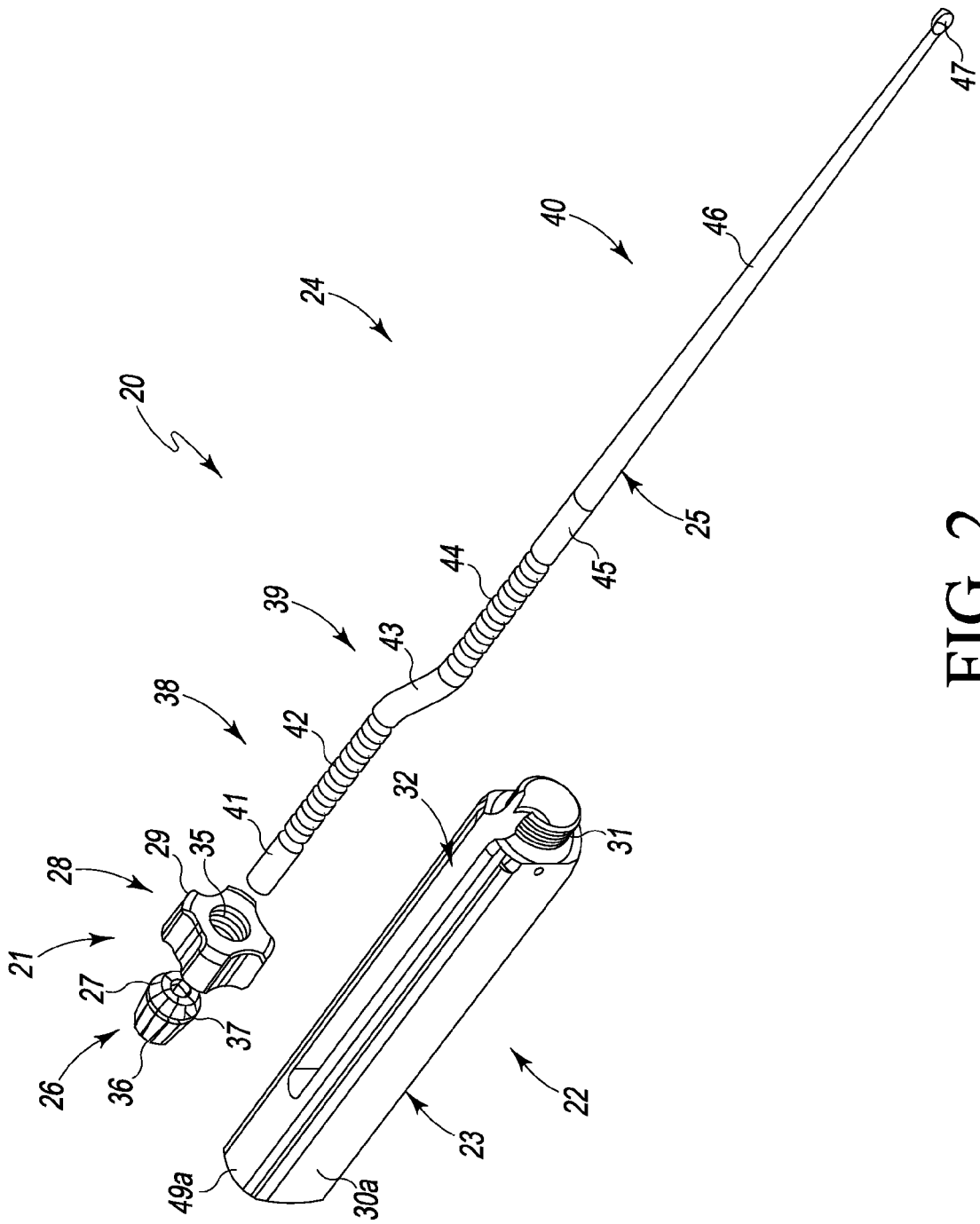
FIG. 2 is an exploded view of the surgical instrument of FIG. 1 illustrating its component parts.
Figure 7:
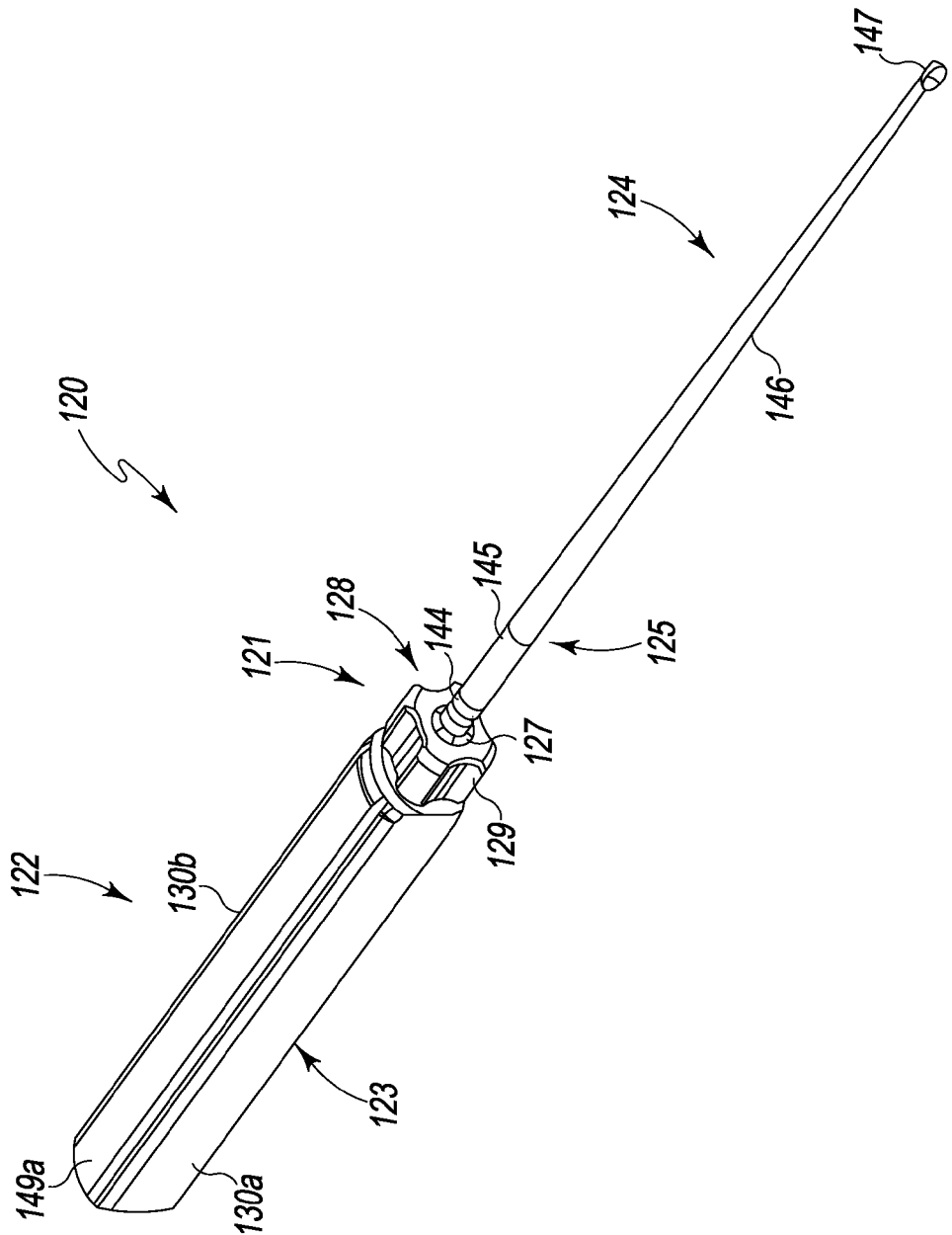
FIG. 7 is an isometric view of another exemplary embodiment of a modular telescoping surgical instrument.
Figure 8:
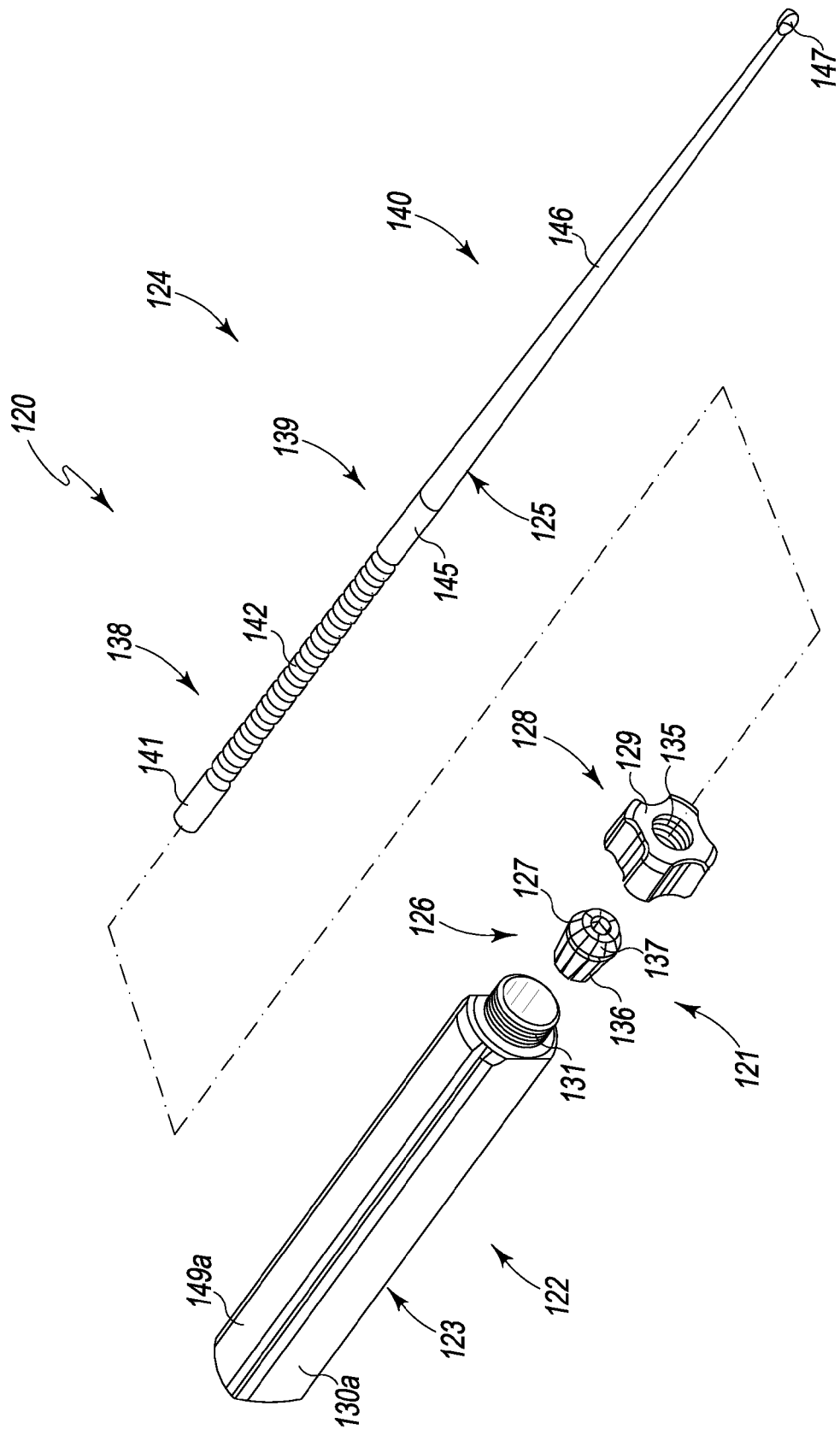
FIG. 8 is an exploded view of the surgical instrument of FIG. 7 illustrating its component parts.
Figure 11:
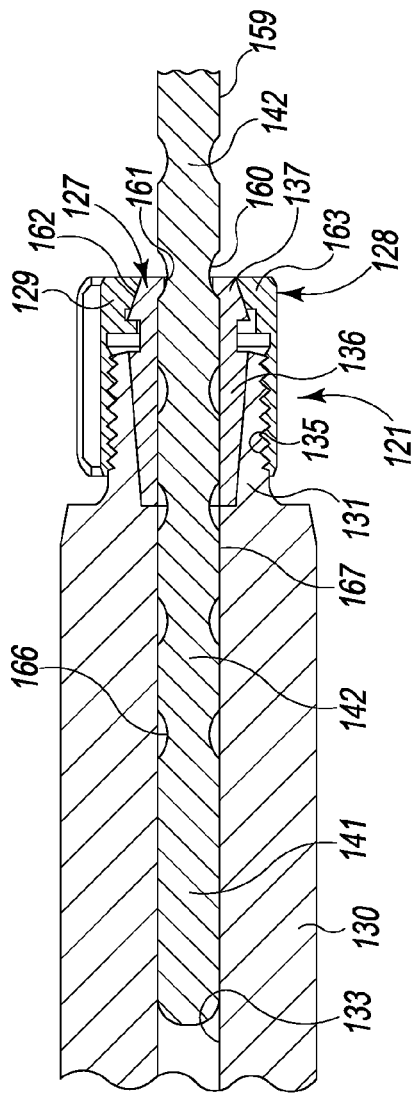
FIG. 11 is an enlarged sectional view of a front portion of the handle and a rear portion of the working end of the surgical instrument of FIG. 7, particularly illustrating the manner in which the rear portion of the working end is received in the front portion of the handle.
Figure 12:
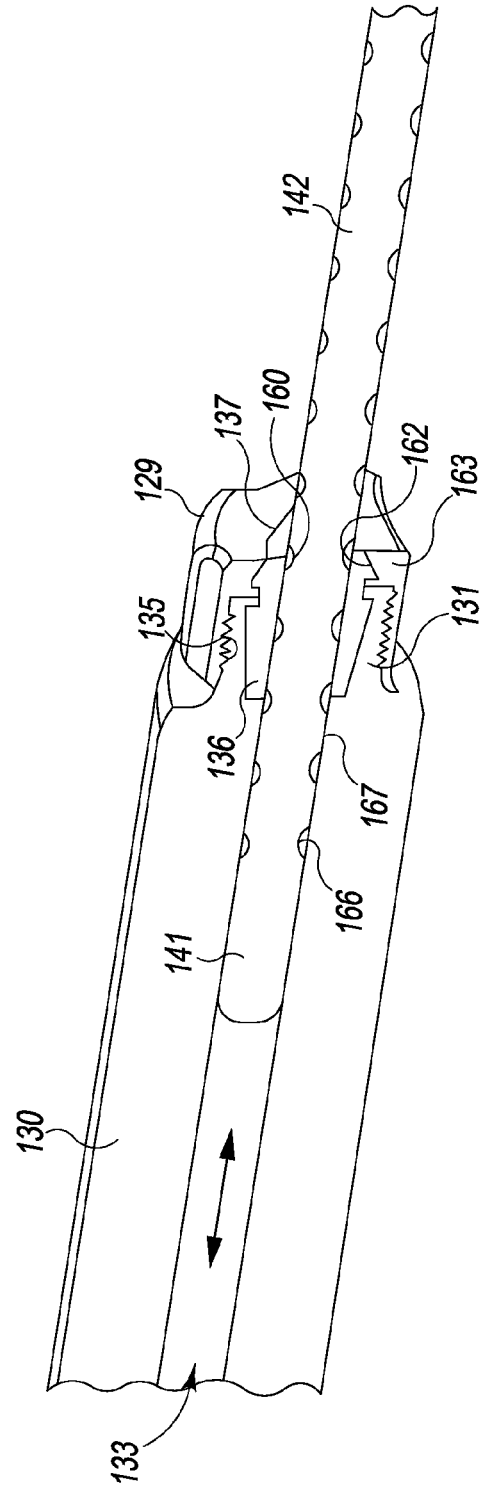
FIG. 12 is an enlarged side sectional view of the front portion of the handle and the rear end of the working end of FIG. 11 particularly illustrating the manner in which the rear portion of the working end is received in the front portion of the handle.
Figure 15:
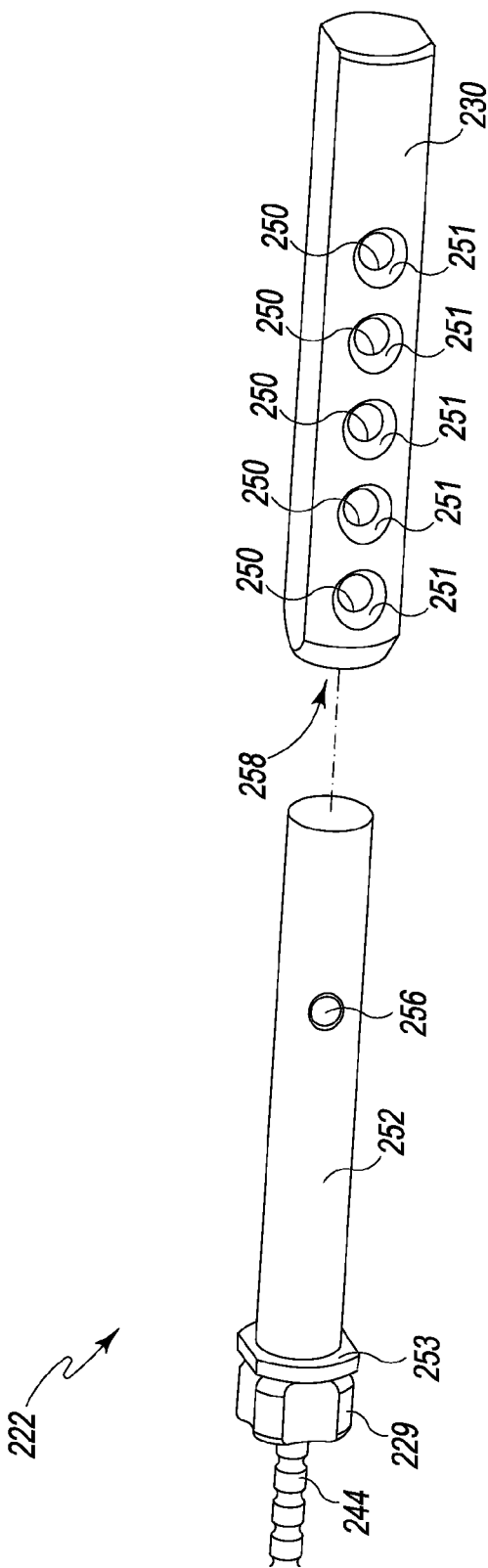
FIG. 15 is an exploded view of two components of the length adjustable handle of FIG. 13.

A detailed description of the features, functions and/or configuration of the components depicted in the various figures will now be presented. It should be appreciated that not all of the features of the components of the figures are necessarily described. Some of these non discussed features as well as discussed features are inherent from the figures. Other non discussed features may be inherent in component geometry and/or configuration.

DETAILED DESCRIPTION OF THE EMBODIMENTS

Referring to FIGS. 1-4, there is depicted an exemplary embodiment of a modular, telescoping surgical instrument (surgical instrument) 20 fashioned in accordance with the principles presented. The surgical instrument 20 is used for various surgical procedures such as orthopedic procedures, but is not limited thereto. The surgical instrument 20 is made from surgical grade materials such as are known in the art unless otherwise indicated.

The surgical instrument 20 has a handle 22, a working end 24, and a retention mechanism 21. The working end 24 is length adjustable relative to the handle 22 and is fixable in position relative to the handle 22 via the retention mechanism 21. For further configuration flexibility, the surgical instrument 20 also provides for the working end 24 to be convertible between a bayonet version and a non-bayonet version. In the non-bayonet version as shown in FIGS. 1-4, a front portion 40 of the working end 24 extends outwardly from a central point of a proximate end of the handle 22, in like manner to a typical screw driver, awl or the like. A longitudinal axis of the front portion 40 is thus co-axial with a central longitudinal axis of the handle 22. In the bayonet version as shown in FIGS. 5-6, the front portion 40 of the working end 24 extends outwardly from an off-central (off-center) point of the proximate end of the handle 22. The longitudinal axis of the front portion 40 thus being parallel to the central longitudinal axis of the handle 22.

The working end 24 comprises an elongated body or shaft 25 of a generally, but not necessarily, circular cross section since shafts of other cross sections may be used and are contemplated. The shaft defines a rear portion 38, a middle portion 39, and a front portion 40. The rear portion 38 has an end 41 that is also the distal end of the shaft 25, and a configured section 42 along a length of a proximate area of the rear portion 38 between the end 41 and the middle portion 39. The configured section 42 is formed by a plurality of circular grooves 66 on the surface of the configured section 42 that are axially spaced apart from one another to form ridges 67 between the grooves 66. As explained further below, the retention mechanism 21 interacts with a groove 66 and adjacent ridges 67 to fix the shaft 25 onto the handle 22 (when the surgical instrument is in the bayonet version). Of course, other configurations may be used for the configured section 42.

The middle portion 39 includes a crook, bend, curve or the like 43 that connects the rear portion 38 with the front portion 40. The crook 43 is angled such that a central longitudinal axis of the front portion 40 is parallel to a central longitudinal axis of the rear portion 38. The crook 43 shown in the figures has an angle of approximately 45°. Angles can range between 0° and 90°. The angle of the crook or bend determines the amount of axial offset between the longitudinal axes of the front and rear portions. In addition to the configuration of the handle 22, the configuration of the working end allows the surgical instrument 20 to convert between the bayonet/non-bayonet versions.

The working end 24 further includes a configured section 44 along a length of the distal area of the front portion 40 between the middle portion 39 and a working tool or tip 47. The configured section 44 is formed by a plurality of circular grooves 60 on the surface of the configured section 44 that are axially spaced apart from one another to form ridges 59 between the grooves 60. As explained further below, the retention mechanism 21 interacts with a groove 60 and adjacent ridges 59 to fix the shaft 25 onto the handle 22 (when the surgical instrument is in the non-bayonet version). Of course, other configurations may be used for the configured section 42. The front portion 40 has a proximate section 46 that tapers from the middle section 39 to a tool or tip 47. The proximate section 46 however, may not taper if desired. The tool or tip 47 may be any type of surgical tool or tip.

The handle 22 is defined by a generally longitudinally elongated, rectangular body 23 defining first and second elongated, rectangular sides 30a, 30b, and first and second elongated, slightly arched top and bottom sides 49a, 49b, it being appreciated that the nomenclature first and second, and top and bottom are arbitrary here and throughout unless otherwise indicated. A slot 32 is formed in the top side 49a that extends from proximate a distal end of the body 23 to a threaded neck 31 of the body 23. As seen, the slot 32 extends through the threaded neck 31. The slot 32 is configured to receive the rear portion 38 of the working end 24 when the surgical instrument 20 is in the non-bayonet version as depicted in FIGS. 1, 3 and 4. The slot 32 is configured at a proximate end such that a slope 48 is defined which widens the end of the slot 32 at the proximate end of the body 23. The slope 48 has an angle that approximates the angle of the crook 43 to act as a stop against rearward longitudinal travel of the rear portion 38 of the working end 24. The length and configuration of the slot 32 is sized to allow the rear portion 38 sufficient room to longitudinally move therein in order to provide length adjustment of the working end 24 relative to the handle 22 when the surgical instrument 20 is in the non-bayonet version or mode.

The handle body 23 further includes a bore 33 that extends from an opening in the slope 48 towards the distal end of the body 23 and parallel to the slot 32. The bore 33 extends along a central or middle longitudinal axis of the body 23. The bore 32 is dimensioned to allow longitudinal reception of the rear portion 38 of the working end 24 when the surgical instrument is in the bayonet version (see FIGS. 5-6). The length and configuration of the slot 33 is sized to allow the rear portion 38 sufficient room to longitudinally move therein in order to provide length adjustment of the working end 24 relative to the handle 22 when the surgical instrument 20 is in the bayonet version or mode.

The retention portion 21 that temporarily retains the working end 24 to the handle 22 comprises a constrictor in the form of a collet 26 and a threaded knob or cap 28. Other types of retention mechanisms may be used and are contemplated. The collet 26 is defined by a generally barrel shaped body 27 having a central bore surrounded by a plurality of longitudinal arms 36 at a rear end thereof and a plurality of front prongs 37. The collet 26 is dimensioned for reception in the tapered interior of the threaded neck 31 of the body 23. The knob 28 is defined by an annular, knobby body 29 having a threaded bore 35. The threaded bore 35 of the body 29 is sized for threaded reception onto the threaded neck 31. The collet 26, the neck 31 of the handle 22, and the knob 28 interact to temporarily fix the longitudinal position of the working end 24 relative to the handle 22 and thus the length that the working end 32 extends from the handle 22.

As seen in FIGS. 3 and 4, the working end 24 is shown in a fixed position in and relative to the handle 22. The working end 24 is in a nearly fully extended position. The collet 26 is situated in the neck 31 with a section of the working end 24 extending through the collet 26, a remaining distal portion of the working end (e.g. the rear portion 38) received in the handle 22. The knob 28 is received on the neck 31. As the knob 28 is threadedly received onto the neck, an angled interior surface 63 of the knob 28 abuts and presses against angled outer surfaces 61 of the front prongs 37 of the collet 26. This presses the collet 26 into the tapered interior of the neck 31. As the longitudinal arms 36 of the collet 26 press against the tapered interior wall of the neck 31, the longitudinal arms 36 are radially compressed against the respective portion of the working end 24. Interior lips 62 of the front prongs 37 are received in a groove 60 of the configured section 44 with a ridge 59 on either side. These features temporarily fix the working end 24 to the handle 22.

Referring to FIGS. 5 and 6, the surgical instrument 20 is shown in the bayonet version. When in the bayonet version, the rear portion 38 of the working end 24 extends into the central bore 33. The configured section 42 is received in and by the collet 26 in like manner as described above. The working end 24 of FIGS. 5 and 6 is shown in a nearly fully retracted position wherein the length of the working end 24 that extends from the handle 22 is at a near minimum. Extending the working end 24 from the handle 22 lengthens the length of the working end 24 that extends from the handle 22.

Referring to FIGS. 7-12, there is depicted another exemplary embodiment of a modular, telescoping surgical instrument (surgical instrument) 120 fashioned in accordance with the principles presented. The surgical instrument 120 is used for various surgical procedures such as orthopedic procedures, but is not limited thereto. The surgical instrument 120 is made from surgical grade materials such as are known in the art unless otherwise indicated. The surgical instrument 120 is similar in form and function to the surgical instrument 20, but provides length adjustment only of the working end 124 relative to the handle 122. As such, where the components, features and the like of the surgical instrument 120 are the same or similar to the corresponding components, features and the like of the surgical instrument 20, the components, features and the like of the surgical instrument 120 have been likewise numbered by adding 100 to the numbered components, features and the like of the surgical instrument 20.

The handle body 123 differs from the handle 22 by having only a single, central bore 133. The retention mechanism 121 may be, and is shown as, the same type of mechanism as the retention mechanism 121 of the surgical instrument 20. The working end 24 differs slightly since the middle portion 139 is straight between the rear portion 138 and the front portion 140 of the working end 124. As such, the longitudinal axis of the front portion 140 is co-axial with the longitudinal axis of the rear portion 138. This is a non-bayonet version. The working end includes only a single configured section (i.e. configured section 142) at the rear portion 138. The front portion 140 has a proximate section 146 that tapers from the middle section 139 to a tool or tip 147. The proximate section 146 however, may not taper if desired. The tool or tip 147 may be any type of surgical tool or tip.

As shown in FIGS. 9 and 10, the working end 124 of the surgical instrument 120, like the working end 24 of the surgical instrument 20, is adjustable in length relative to the handle 122. FIG. 9 depicts a near fully retracted working end 124 relative to the handle 122 wherein the length L1 represents the length of the working end 124 that extends beyond the handle 122, while length D1 represents the length of the working end 124 that extends into the handle 122, the total length L1+D1=the longitudinal length of the working end 124. FIG. 10 depicts a near fully extended working end 124 relative to the handle 122 wherein the length L2 represents the length of the working end 124 that extends beyond the handle 122, while length D2 represents the length of the working end 124 that extends into the handle 122, the total length L2+D2=the longitudinal length of the working end 124. The working end 24 of the surgical instrument 20 is length adjustable in the same manner.

Figure 16:
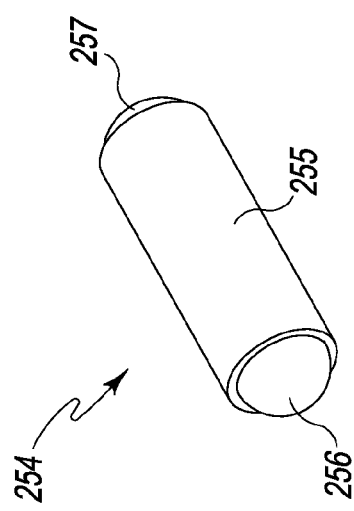
FIG. 16 is an enlarged isometric view of an adjustment pin of the length adjustable handle of FIG. 13.

Referring to FIG. 13-16, an alternate version of a handle 222 that can used with the surgical instruments 20, 120 is shown. The handle 222 is, of itself, also length adjustable. While not seen, a retention mechanism as described herein is situated at the proximate end 253 of the handle 222, the knob 229 of which is shown. The configured section 244 of the working end 224 is shown extending from the handle 222. The handle 222 includes a shaft 252 having an interior that accommodates the working end and retention mechanism as described herein. A double-headed catch pin 254 is situated in a near distal end of the shaft 252. As seen in the enlargement of FIG. 16, the catch pin 254 has a cylindrical body 255 having a first ball bearing 256 in one end of the cylindrical body 255, and a second ball bearing 257 in another end of the cylindrical body 255. The first and second ball bearings 256, 257 are spring-loaded, or otherwise, such as is known in the art.

The handle 222 further includes a sleeve 230 having an opening 258 in an end thereof. The opening 258 of the sleeve 230 is sized for reception on the shaft 252. The sleeve 230 has a plurality of holes on both sides thereof that have tapered openings 251, the openings sized such that a ball bearing (256, 257) may extend through but be caught thereby. The tapered openings allow easy access to bias the ball bearings 256, 257 inward to slide the sleeve 230 along the shaft 252 in order to change the overall length of the handle 222. Of course, a single ball bearing/detent structure may be used.

FIG. 13 shows the handle 222 in a minimum length position. The ball bearing 256 extends into the distal-most hole 250 of the handle. FIG. 14 shows the handle 222 in a near maximum length position. The ball bearing 256 extends in into the near proximate-most hole 250 of the handle 222.

While the invention has been illustrated and described in detail in the drawings and foregoing description, the same is to be considered as illustrative and not restrictive in character, it being understood that preferred embodiments have been shown and described and that all changes and modifications that come within the spirit of the invention are desired to be protected.

What is claimed is:

1. A surgical instrument comprising:
   a handle having a configured opening at a front end thereof, a first axial bore extending longitudinally into the handle from the configured opening offset from a center longitudinal axis of the handle, and a second axial bore extending longitudinally into the handle from the configured opening coaxial with the center longitudinal axis of the handle;
   a working end having a rear portion, an angled middle portion, and a front portion adapted to carry a working tool, the rear portion configured for reception in the first or second axial bore wherein when the rear portion of the working end is received in the first axial bore the front portion of the working end extends from the front end of the handle co-axial with a center longitudinal axis of the handle, and when the rear portion of the working end is received in the second axial bore the front portion of the working end extends from the front end of the handle at a longitudinal axis of the handle that is offset from the center longitudinal axis of the handle; and
   a retention mechanism configured to interact with the configured opening of the handle and the working end to fix a longitudinal position of the rear portion of the working end in the first or second axial bore of the handle.

2. The surgical instrument of claim 1, wherein:
   the configured opening includes a slot and threading; and
   the retention mechanism includes a constrictor configured for reception in the configured opening with a portion of the working end extending through the constrictor, and a threaded knob configured for reception on the configured opening threading, the threaded knob configured to cause the configured opening to compress the constrictor which compresses the constrictor against the portion of the working end extending through the constrictor to fix the axial position of the working end relative to the handle.

3. The surgical instrument of claim 2, wherein the constrictor comprises a collet.

4. The surgical instrument of claim 2 wherein the handle has a first axial slot that is in communication with the first axial bore of the handle and the slot of the configured opening.

5. The surgical instrument of claim 4, wherein the configured opening is integral with the handle.

6. The surgical instrument of claim 1, wherein the handle is length adjustable.

7. The surgical instrument of claim 1, wherein the working end includes a first plurality of grooves about the rear portion of the working end, and a second plurality of grooves about the middle portion of the working end.

8. A surgical instrument comprising:
   an elongated handle having a configured opening at a front end thereof, a first axial bore extending longitudinally into the handle from the configured opening offset from a center longitudinal axis of the handle, and a second axial bore extending longitudinally into the handle from the configured opening coaxial with the center longitudinal axis of the handle;
   a working end having a rear portion, an angled middle portion, and a front portion adapted to carry a working tool, the front portion axially offset from the rear portion, the rear portion configured for reception in the first or second axial bore wherein when the rear portion of the working end is received in the first axial bore the front portion of the working end extends from the front end of the handle co-axial with a center longitudinal axis of the handle, and when the rear portion of the working end is received in the second axial bore the front portion of the working end extends from the front end of the handle at a longitudinal axis of the handle that is offset from the center longitudinal axis of the handle; and
   a collet and knob configured to interact with the configured opening of the handle and the working end to fix a longitudinal position of the rear portion of the working end in the first or second axial bore of the handle.

9. The surgical instrument of claim 8, wherein the handle has a first axial slot that is in communication with the first axial bore of the handle and the slot of the configured opening.

10. The surgical instrument of claim 9, wherein the configured opening is integral with the handle.

11. The surgical instrument of claim 8, wherein the handle is length adjustable.

12. The surgical instrument of claim 1, wherein the working end includes a first plurality of grooves about the rear portion of the working end, and a second plurality of grooves about the middle portion of the working end.

* * * * *